US011666299B2

(12) United States Patent
Baruth et al.

(10) Patent No.: US 11,666,299 B2
(45) Date of Patent: Jun. 6, 2023

(54) CONTROLLING A MEDICAL X-RAY DEVICE

(71) Applicant: Siemens Healthcare GmbH, Erlangen (DE)

(72) Inventors: Oliver Baruth, Herzogenaurach (DE); Philipp Bernhardt, Forchheim (DE)

(73) Assignee: Siemens Heatlhcare GmbH, Erlangen (DE)

( * ) Notice: Subject to any disclaimer, the term of this patent is extended or adjusted under 35 U.S.C. 154(b) by 196 days.

(21) Appl. No.: 17/152,350

(22) Filed: Jan. 19, 2021

(65) Prior Publication Data

US 2021/0228173 A1    Jul. 29, 2021

(30) Foreign Application Priority Data

Jan. 27, 2020    (DE) .......................... 102020200906.6

(51) Int. Cl.
*A61B 6/00*    (2006.01)
(52) U.S. Cl.
CPC ................ *A61B 6/54* (2013.01); *A61B 6/463* (2013.01); *A61B 6/467* (2013.01); *A61B 6/5205* (2013.01)
(58) Field of Classification Search
CPC ......... A61B 6/54; A61B 6/5205; A61B 6/467; A61B 6/463; A61B 5/7289; A61B 5/5288;

(Continued)

(56) References Cited

U.S. PATENT DOCUMENTS 8,311,308 B2    11/2012   Chen
8,433,115 B2     4/2013   Chen
(Continued)

FOREIGN PATENT DOCUMENTS

DE    102010028446 A1    11/2011
DE    102011090047 A1     7/2013
(Continued)

OTHER PUBLICATIONS

German Office Action for German Application No. 10 2020 200 906.6 dated Oct. 19, 2020.

*Primary Examiner* — Don K Wong
(74) *Attorney, Agent, or Firm* — Lempia Summerfield Katz LLC

(57) ABSTRACT

The disclosure relates to a method for controlling a medical X-ray device. The method includes: acquiring at least one X-ray image of a region of examination of an object undergoing examination by the medical X-ray device, wherein a medical object is arranged in the region of examination; generating an object image based on the at least one X-ray image; and establishing a determinability parameter, for assessing the determinability of the medical object based on the object image. The method is carried out iteratively, beginning with the acquiring of an X-ray image, until a termination condition occurs based on the most recently established determinability parameter. The disclosure furthermore relates to a computer-implemented method for providing a trained function, a computer-implemented method for providing a further trained function, a medical X-ray device, a training unit, a computer program product, and a computer-readable storage medium.

14 Claims, 10 Drawing Sheets

(58) Field of Classification Search
CPC ....... A61B 6/541; A61B 6/469; A61B 6/5235; A61N 2005/1061; A61N 2005/1062; A61N 5/1037; A61N 5/1048; A61N 5/1049; G06T 5/50
See application file for complete search history.

(56) References Cited

U.S. PATENT DOCUMENTS

| | | | |
|---|---|---|---|
| 8,571,639 B2 * | 10/2013 | Mostafavi | A61B 6/504 600/407 |
| 10,278,667 B2 | 5/2019 | Iijima | |
| 2011/0268341 A1 | 11/2011 | Boese | |
| 2014/0304206 A1 | 10/2014 | Lee | |
| 2015/0039553 A1 | 2/2015 | Becker | |
| 2017/0281115 A1 | 10/2017 | Julien | |
| 2019/0102621 A1 | 4/2019 | Flohr | |

FOREIGN PATENT DOCUMENTS

| | | |
|---|---|---|
| DE | 102017217543 A1 | 4/2019 |
| EP | 2790583 B1 | 5/2016 |

* cited by examiner

CONTROLLING A MEDICAL X-RAY DEVICE

The present patent document claims the benefit of German Patent Application No. 10 2020 200 906.6, filed Jan. 27, 2020, which is hereby incorporated by reference in its entirety.

TECHNICAL FIELD

The disclosure relates to a method for controlling a medical X-ray device, a computer-implemented method for providing a trained function, a computer-implemented method for providing a further trained function, a medical X-ray device, a training unit, a computer program product, and a computer-readable storage medium.

BACKGROUND

For monitoring a treatment, (e.g., cardiovascular treatment), of an object undergoing examination by imaging, there is a need for reliable and sufficiently high-quality mapping of a region of examination of the object undergoing examination. For the purpose of mapping the region of examination—in particular, a medical object arranged therein, such as a guide wire and/or catheter and/or endoscope and/or laparoscope and/or implant, in particular a stent—rapidly and with the minimum of delay, imaging based on X-rays is frequently used. In this case, for the purpose of enhancing image quality, in particular a signal-to-noise ratio (SNR) and/or contrast-to-noise ratio (CNR), a particularly high dose of X-rays coupled to a short duration of administration is frequently selected. However, in this case, the technical limitations of the X-ray source, (e.g., the X-ray tube), in relation to the maximum possible output are frequently disadvantageous.

As an alternative or in addition, the image quality may be improved by averaging a series of X-ray images. For this purpose, a defined number of X-ray images of the region of examination may be acquired in a temporal sequence. Here, the individual X-ray images of the series are frequently each of an image quality that is insufficient for determining the medical object. Furthermore, the individual X-ray images of the series may each map at least partly differing regions of examination, in particular as a result of movement of at least one part of the object undergoing examination. By retrospectively applying a movement correction and/or registration, and by averaging the series of X-ray images, it is frequently possible to achieve improved image quality in the result image. However, it is disadvantageous here that the defined number of X-ray images to be acquired must be predetermined, and the image quality of the result image is only seen after the entire X-ray dose has been administered. However, different objects undergoing examination frequently need to be adjusted to the number of X-ray images to be acquired, in order to achieve sufficient image quality in the result image.

SUMMARY AND DESCRIPTION

For this reason, the object of the disclosure is to minimize the X-ray dose during mapping of a medical object. The scope of the present disclosure is defined solely by the appended claims and is not affected to any degree by the statements within this summary. The present embodiments may obviate one or more of the drawbacks or limitations in the related art.

The solution to the object will be described below both in relation to methods for controlling a medical X-ray device and also in relation to methods and apparatuses for providing a trained function and methods and apparatuses for providing a further trained function. Here, features, advantages, and alternative embodiments of data structures and/or functions in methods for controlling a medical X-ray device are applicable to analogous data structures and/or functions in methods and apparatuses for providing a trained function and methods and apparatuses for providing a further trained function. In this context, analogous data structures may be characterized by the use of the prefix "training". Moreover, the trained functions that are used in methods for controlling a medical X-ray device may be adjusted and/or provided by methods and apparatuses for providing a trained function and/or methods for providing a further trained function.

In a first aspect, the disclosure relates to a method for controlling a medical X-ray device. Here, in act a), at least one X-ray image of a region of examination of an object undergoing examination is acquired by the medical X-ray device, wherein a medical object is arranged in the region of examination. Furthermore, in act b), an object image is generated based on the at least one X-ray image. Then, in act c), a determinability parameter is established, for the purpose of assessing the determinability of the medical object based on the object image. Furthermore, the proposed method is carried out iteratively, beginning at act a), until a termination condition occurs based on the most recently established determinability parameter.

Here, the at least one X-ray image may include a plurality of image points, in particular, pixels and/or voxels. Advantageously, the at least one X-ray image may map at least in part the region of examination of the object undergoing examination. In this case, the object undergoing examination may be a human and/or animal patient and/or an X-ray phantom. Furthermore, the at least one X-ray image may include a two-dimensional projection mapping and/or a three-dimensional mapping of the region of examination. Furthermore, a plurality of X-ray images may be acquired by the medical X-ray device, wherein the plurality of X-ray images may include at least partly differing acquisition parameters, for example, angulation and/or field of view (FOV). Furthermore, the at least one X-ray image may include metadata, wherein the metadata may include an item of information on acquisition parameters and/or operating parameters and/or physiological parameters of the object undergoing examination, and/or an item of patient information.

Advantageously, the medical object, (e.g., a guide wire and/or catheter and/or endoscope and/or laparoscope and/or implant, in particular a stent), arranged in the region of examination of the object undergoing examination is mapped in the at least one X-ray image.

For the purpose of acquiring the at least one X-ray image of the region of examination of the object undergoing examination that is to be mapped in act a), the medical X-ray device may include an X-ray source and a detector unit. Furthermore, the X-ray source may emit a bundle of X-rays, (e.g., a cone beam and/or a fan beam and/or a parallel beam), wherein the region of examination is illuminated by the bundle of X-rays. When, after interaction with the region of examination of the object undergoing examination that is to be mapped, the X-ray bundle impinges on a surface of the detector unit, the detector unit may provide a signal. Here, the at least one X-ray image may be reconstructed and/or provided based on the signal.

In act b), the object image may be generated based on the at least one X-ray image. Here, advantageously the object image may include a segmented, (e.g., isolated), two-dimensional and/or three-dimensional mapping of the medical object and/or a marker structure, (e.g., a balloon marker), arranged in particular on the medical object. Advantageously, generation of the object image based on the at least one X-ray image may include filtering and/or segmentation and/or identification of the medical object and/or the marker structure. For example, the medical object and/or marker structure may be segmented and/or identified based on a geometric shape, in particular a contour, and/or based on a comparison of image intensity values, in particular with a predetermined threshold value, in the at least one X-ray image.

Advantageously, based on the object image, a determinability parameter may be established in act c). Here, the determinability parameter may advantageously include an item of information on confidence in and/or an image quality of the object image. Here, the determinability parameter may include at least one value, in particular a numerical value, that assesses the determinability of the medical object from the at least one X-ray image, in particular when the object image is generated in act b). In particular, the determinability parameter may include an item of information on the confidence in filtering and/or segmenting and/or identifying the medical object and/or the marker structure in the at least one X-ray image. Furthermore, the determinability parameter may include an item of information on the image quality of the object image and/or the at least one X-ray image, (e.g., a contrast-to-noise ratio and/or a signal-to-noise ratio and/or an image definition). Moreover, the determinability parameter may include an item of information on how prominent the medical object is in the at least one X-ray image and/or the object image. In this context, the item of information on how prominent the medical object is in the at least one X-ray image and/or the object image may include an intensity ratio and/or a contrast value between the image points that correspond to mapping of the medical object and other image points.

Furthermore, the determinability parameter may include a determinability matrix that is two-dimensional and/or three-dimensional, wherein the values of the determinability matrix assess the determinability of the medical object in each case in at least one sub-region of the object image. In particular, the determinability matrix may be established image point by image point.

The termination condition may advantageously include a comparison of the determinability parameter that was most recently established in act c)—in particular during the current iteration—with a predetermined threshold value. If the determinability parameter includes a plurality of values and/or a determinability matrix, the termination condition may include a comparison of the plurality of values and/or the individual values of the determinability matrix with the predetermined threshold value. Here, the proposed method for controlling the medical X-ray device may be carried out iteratively, beginning at act a), until the termination condition occurs based on the most recently established determinability parameter. Moreover, the termination condition may occur if the determinability parameter exceeds and/or falls below and/or reaches the predetermined threshold value. Furthermore, the termination condition may include a maximum number of iterations, with the termination condition occurring if the maximum number of iterations is reached and/or exceeded.

In particular, if X-rays are emitted by the X-ray source in pulses over time, it is possible for the X-ray source to emit respectively a time-limited X-ray pulse and/or a defined number of X-ray pulses in act a). In this case, if the termination condition occurs, advantageously the radiation may be terminated—in particular the emission of X-rays by the X-ray source in pulses over time may be stopped.

Furthermore, in the event of acts a) to c) being carried out iteratively, advantageously in each case at least one determinability parameter may be established for the at least one X-ray image—in particular the most recently acquired X-ray image based on the object image.

Furthermore, generation of the object image in act b) during iterative carrying out of the proposed method may additionally be based on at least one X-ray image that was acquired in a previous iteration. As a result, advantageously the determinability parameter may be improved during the iterative carrying out of acts a) to c).

Because, after each acquisition of at least one X-ray image, an assessment is made of the determinability of the medical object, advantageously the duration of examination and/or the X-ray dose administered may be reduced to the minimum required for determining the medical object.

In a further advantageous embodiment of the proposed method for controlling a medical X-ray device, the object image may be generated by an in particular weighted and/or adaptive averaging of at least a subset of the X-ray images acquired hitherto.

During an iterative carrying out of acts a) to c), the object image may be generated in act b) advantageously based on at least one subset of the X-ray images acquired hitherto, in particular respectively in act a) of the iterations hitherto. In this case, the at least one subset may be a subset that includes at least one or all of the X-ray images acquired hitherto. Furthermore, the object image may be generated based on a plurality of subsets of the X-ray images acquired hitherto.

In this case, generation of the object image in act b) may include an in particular weighted and/or adaptive averaging of the at least one subset of the X-ray images that have been acquired hitherto. During a weighted averaging of the at least one subset of the X-ray images acquired hitherto, the X-ray images may advantageously be weighted in dependence on their respective image quality, in particular a single-to-noise ratio and/or a contrast-to-noise ratio. Furthermore, adaptive averaging may be performed in at least one image region of the X-ray images that includes imaging of the medical object. Here, averaging of the at least one subset of the X-ray images acquired hitherto may be performed in particular by the detector unit of the medical X-ray device, for example, by binning at least some of the detector pixels.

If the object image is generated based on a plurality of subsets of the X-ray images acquired hitherto, then in each case an intermediate image may be generated for each of the subsets, for example, by a weighted and/or adaptive averaging, wherein the object image may be generated by a weighted and/or adaptive averaging of the intermediate images.

As a result, advantageously an improvement in the image quality of the object image, in particular the determinability parameter, may be achieved.

In a further advantageous embodiment of the proposed method for controlling a medical X-ray device, the at least one subset of the X-ray images acquired hitherto for the purpose of generating the object image may be determined based on the determinability parameter.

Advantageously, during an iterative carrying out of acts a) to c), in each case at least one determinability parameter may be established for the at least one X-ray image, in particular the X-ray image most recently acquired, based on the object image. In this case, the at least one subset of the X-ray images acquired hitherto for the purpose of generating the object image in act b) may furthermore be determined based on the at least one determinability parameter. In particular, determining the at least one subset of the X-ray images that have been acquired hitherto may include a comparison of the determinability parameters of the X-ray images acquired hitherto with a threshold value, in particular an average of the determinability parameters. If the determinability parameter assesses the determinability of the medical object based on the object image in such a way that the value of the determinability parameter increases monotonically in relation to the determinability, then advantageously it is possible to include only the X-ray images acquired hitherto in the at least one subset for the purpose of generating the object image whereof the determinability parameters have a value above the threshold value—in particular the average value of the determinability parameters. Furthermore, the X-ray images that include a determinability parameter with a value below the threshold, in particular below the average value of the determinability parameters, may be excluded from the at least one subset for the purpose of generating the object image. When there is a monotonically decreasing relationship between the value of the determinability parameter and the determinability of the medical object, the comparison may be adjusted analogously.

As a result, it is advantageously possible to achieve an improvement, in particular an enhancement, in the determinability parameter of the current iteration. Furthermore, X-ray images that include image artifacts and/or noise and/or motion artifacts may advantageously be excluded from the at least one subset for the purpose of generating the object image.

In this case, determining the at least one subset for the purpose of generating the object image may further include taking into account the possible permutations of the X-ray images that have been acquired hitherto with the respective determinability parameters.

In a further advantageous embodiment of the proposed method for controlling a medical X-ray device, the termination condition may include a comparison of the determinability parameter with a predetermined threshold value. Here, the comparison of the determinability parameter—in particular of at least one value of the determinability parameter—with the predetermined threshold value may include a difference and/or a quotient and/or a scalar product. Advantageously, the threshold value may be predetermined such that, when the termination condition occurs, the medical object is fully determinable, (e.g., being detectable and/or identifiable and/or locatable), in the object image, (e.g., by a member of the operating personnel).

As a result, advantageously the duration of examination and/or the X-ray dose administered may be reduced.

In a further advantageous embodiment of the proposed method for controlling a medical X-ray device, generation of the object image may include a movement correction and/or registration of the at least one X-ray image. In this case, the movement correction and/or the registration may advantageously include a rigid and/or non-rigid transformation of the at least one X-ray image. If a plurality of X-ray images is acquired in act a) and/or if acts a) to c) are carried out iteratively, the plurality of X-ray images may be registered. In this case, the registration may be carried out based on geometric and/or anatomical landmarks, and/or a marker structure arranged on the medical object. As a result, it is possible to achieve an improvement in the image quality of the object image, which is advantageously generated based on the at least one subset of the X-ray images acquired hitherto. Furthermore, as a result it is advantageously possible to improve the determinability parameters.

Moreover, the movement correction may be carried out based on geometric and/or anatomical landmarks in the at least one X-ray image. As an alternative or in addition, the movement correction may be carried out based on a physiological signal, such as a heart graph and/or respiratory graph, from the object undergoing examination. Furthermore, the physiological signal may be derived from the at least one X-ray image and/or metadata therein.

In a further advantageous embodiment of the proposed method for controlling a medical X-ray device, the determinability parameter may be established in act c) by applying a trained function to input data. Here, the input data may be based on the object image. Moreover, at least one parameter of the trained function may be based on a comparison of a training determinability parameter with a comparison determinability parameter.

The trained function may advantageously be trained by a machine learning method. In particular, the trained function may be a neural network, (e.g., a convolutional neural network (CNN)), or a network including a convolutional layer.

The trained function maps input data onto output data. Here, the output data may further depend on one or more parameters of the trained function. The one or more parameters of the trained function may be determined and/or adjusted by a training act. Determination and/or adjustment of the one or more parameters of the trained function may be based on a pair including training input data and associated training output data, wherein the trained function is applied to the training input data for the purpose of generating training mapping data. In particular, determination and/or adjustment may be based on a comparison of the training mapping data with the training output data. In general, a trainable function—that is to say a function having one or more parameters that have not yet been adjusted—is also designated a trained function.

Other terms for trained functions include the following: trained mapping rule; mapping rule with trained parameters; function with trained parameters; algorithm based on artificial intelligence; machine learning algorithm. An example of a trained function is an artificial neural network wherein the edge weights of the artificial neural network correspond to the parameters of the trained function. Instead of the term "neural network," the term "neural net" may also be used. In particular, a trained function may also be a deep neural network (or deep artificial neural network). A further example of a trained function is a support vector machine, and other machine learning algorithms may also be used as a trained function.

The trained function may be trained by backpropagation. First, training mapping data may be determined by applying the trained function to training input data. Then, a discrepancy between the training mapping data and the training output data may be established by applying an error function to the training mapping data and the training output data. Furthermore, at least one parameter (e.g., a weighting) of the trained function, in particular the neural network, may be adjusted iteratively based on a gradient of the error function in relation to the at least one parameter of the trained function. As a result, the discrepancy between the training mapping data and the training output data may advantageously be minimized during training of the trained function.

Advantageously, the trained function, in particular the neural network, includes an input layer and an output layer. In this arrangement, the input layer may be formed for the purpose of receiving input data. Furthermore, the output layer may be formed for the purpose of providing mapping data. Here, the input layer and/or the output layer may each include a plurality of channels, in particular neurons.

At least one parameter of the trained function may be based on a comparison of a training determinability parameter with a comparison determinability parameter. In this case, the training determinability parameter and/or the comparison determinability parameter may advantageously be determined as part of a proposed computer-implemented method for providing a trained function (this method will be explained later in the description). In particular, the trained function may be provided by an embodiment of the proposed computer-implemented method for providing a trained function.

As a result, it is possible to improve assessment of the determinability of the medical object, in particular identification and/or location and/or detectability, in the object image.

In a further advantageous embodiment of the proposed method for controlling a medical X-ray device, the object image may be generated in act b) by applying a further trained function to further input data. Here, the further input data may be based on the at least one X-ray image. Furthermore, at least one parameter of the further trained function may be based on a comparison of a further training object image with a comparison object image.

The advantages and properties of the further trained function described above correspond substantially to the advantages and properties of the trained function. The features, advantages, or alternative embodiments that are mentioned in relation to the trained function may likewise apply to the further trained function, and vice versa.

At least one parameter of the further trained function may be based on a comparison of a further training object image with a comparison object image. In this case, the further training object image and/or the comparison object image may advantageously be determined as part of a proposed computer-implemented method for providing a further trained function (this method will be explained later in the description). In particular, the further trained function may be provided by an embodiment of the proposed computer-implemented method for providing a further trained function.

This may enable particularly reliable and robust generation of the object image.

In a further advantageous embodiment of the proposed method for controlling a medical X-ray device, the further trained function may moreover be configured for establishing the determinability parameter. Here, at least one further parameter of the further trained function may be based on a comparison of a training determinability parameter with a comparison determinability parameter.

The at least one further parameter of the further trained function may be based on a comparison of a training determinability parameter with a comparison determinability parameter. In this case, the training determinability parameter and/or the comparison determinability parameter may advantageously be determined as part of a proposed computer-implemented method for providing a further trained function (this method will be explained later in the description). In particular, the further trained function may be provided by an embodiment of the proposed computer-implemented method for providing a further trained function.

As a result, assessment of the determinability of the medical object, in particular of identification and/or location and/or detectability, in the object image may be improved.

In a second aspect, the disclosure relates to a computer-implemented method for providing a trained function. Here, in a first act, at least one training X-ray image of a region of examination of an object undergoing examination is received, wherein a medical object is arranged in the region of examination. In a second act, a training object image based on the at least one training X-ray image is generated. Furthermore, in a third act, a comparison determinability parameter is established for assessing the determinability of the medical object based on the training object image. In a fourth act, a training determinability parameter is established by applying the trained function to input data. Here, the input data is based on the at least one training X-ray image. In a fifth act, at least one parameter of the trained function is adjusted based on a comparison of the training determinability parameter with the comparison determinability parameter. After this the trained function is provided.

Receiving the at least one training X-ray image may include detecting and/or reading from a computer-readable data store and/or receiving from a data storage unit such as a database. Furthermore, the at least one training X-ray image may be provided by a providing unit of a medical X-ray device.

The at least one training X-ray image may have all the properties of the at least one X-ray image that have been described in relation to the method for controlling a medical X-ray device, and vice versa. In particular, the at least one training X-ray image may be an X-ray image. Furthermore, the at least one training X-ray image may be simulated.

Here, the at least one training X-ray image may include a plurality of image points, in particular pixels and/or voxels. Advantageously, the at least one training X-ray image may at least partly map the region of examination of the object undergoing examination. In this case, the at least one training X-ray image may include a two-dimensional projection mapping and/or a three-dimensional mapping of the region of examination. Furthermore, a plurality of training X-ray images may be received, wherein the plurality of training X-ray images may include at least partly differing acquisition parameters, such as angulation and/or an acquisition region. Furthermore, the at least one training X-ray image may include metadata, wherein the metadata may include an item of information on acquisition parameters and/or operating parameters and/or physiological parameters of the object undergoing examination, and/or an item of patient information.

Advantageously, the medical object, (e.g., a guide wire and/or catheter and/or endoscope and/or laparoscope and/or implant, in particular a stent), that is arranged in the region of examination of the object undergoing examination, may be mapped in the at least one training X-ray image.

In this case the medical object described in this context, which is mapped in the at least one training X-ray image, may be similar to or different from the medical object that is mapped in the at least one X-ray image and that has been described in relation to the method for controlling a medical X-ray device, and vice versa. Analogously, the object undergoing examination and/or the region of examination in which the medical object is arranged, and which is mapped in the at least one training X-ray image, may be the same as or different from the object undergoing examination and/or the region of examination that has been described in relation to the method for controlling a medical X-ray device, and vice versa.

In a manner analogous with generation of the object image in act b) of the proposed method for controlling a medical X-ray device, the training object image may be generated based on the at least one training X-ray image. The training object image may have all the properties of the object image that have been described in relation to the method for controlling a medical X-ray device, and vice versa.

In this case, the training object image may advantageously include a segmented, (e.g., isolated), two-dimensional and/or three-dimensional mapping of the medical object and/or a marker structure arranged in particular on the medical object. Advantageously, generation of the training object image based on the at least one training X-ray image may include filtering and/or segmenting and/or identification of the medical object and/or the marker structure. For example, the medical object and/or the marker structure may be segmented and/or identified based on a geometric shape, (e.g., a contour), and/or based on a comparison of image intensity values, (e.g., with a predetermined threshold value), in the at least one training X-ray image.

Furthermore, the comparison determinability parameter may be established in a manner analogous with act c) of the proposed method for controlling a medical X-ray device, based on the training object image. The comparison determinability parameter may have all the properties of the determinability parameter that have been described in relation to the method for controlling a medical X-ray device, and vice versa. Furthermore, the comparison determinability parameter may be established by a manual and/or semiautomatic annotation based on the training object image.

By applying the trained function to input data that is based on the at least one training X-ray image, it is advantageously possible to establish the training determinability parameter. Here, at least one parameter of the trained function may be adjusted, based on a comparison of the training determinability parameter with the comparison determinability parameter. Furthermore, it is possible for the comparison to include, for example, a difference and/or a scalar product and/or a quotient.

Provision of the trained function may include storage on a computer-readable storage medium and/or transfer to a providing unit.

Advantageously, using the method proposed here, it is possible to provide a trained function that may be used in an embodiment of the method for controlling a medical X-ray device.

In a third aspect, the disclosure relates to a computer-implemented method for providing a further trained function. Here, in a first act, at least one training X-ray image of a region of examination of an object undergoing examination is received, wherein a medical object is arranged in the region of examination. In a second act, a comparison object image is generated based on the at least one training X-ray image. Furthermore, in a third act, a further training object image is generated by applying the further trained function to further input data. In this case, the further input data is based on the at least one training X-ray image. In a fourth act, at least one parameter of the further trained function is adjusted based on a comparison of the further training object image with the comparison object image. After this, the further trained function is provided.

Receiving the at least one training X-ray image may include detecting and/or reading from a computer-readable data store and/or receiving from a data storage unit such as a database. Furthermore, the at least one training X-ray image may be provided by a providing unit of a medical X-ray device.

In this case, the medical object described in this context, which is mapped in the at least one training X-ray image, may be similar to or different from the medical object that is mapped in the at least one X-ray image and that has been described in relation to the method for controlling a medical X-ray device, and vice versa. Analogously, the object undergoing examination and/or the region of examination in which the medical object is arranged and which is mapped in the at least one training X-ray image may be the same as or different from the object undergoing examination and/or the region of examination that has been described in relation to the method for controlling a medical X-ray device, and vice versa.

The at least one training X-ray image may have all the properties of the at least one X-ray image that have been described in relation to the method for controlling a medical X-ray device, and vice versa. In particular, the at least one training X-ray image may be an X-ray image. Furthermore, the at least one training X-ray image may be simulated.

In a manner analogous with generation of the object image in act b) of the proposed method for controlling a medical X-ray device, the comparison object image may be generated based on the at least one training X-ray image. The comparison object image may have all the properties of the object image that have been described in relation to the method for controlling a medical X-ray device, and vice versa.

By applying the further trained function to the further input data that is based on the at least one training X-ray image, it is advantageously possible to generate the further training object image. Here, at least one parameter of the further trained function may be adjusted, based on a comparison of the further training object image with the comparison object image. Furthermore, it is possible for the comparison to include, for example, a difference and/or a scalar product and/or a quotient.

Provision of the further trained function may include storage on a computer-readable storage medium and/or transfer to a providing unit.

Advantageously, using the method proposed here it is possible to provide a further trained function that may be used in an embodiment of the method for controlling a medical X-ray device.

In a further advantageous embodiment of the proposed computer-implemented method for providing a further trained function, a comparison determinability parameter may be established for the purpose of assessing the determinability of the medical object, based on the further training object image. Furthermore, a training determinability parameter may be established by applying the further trained function to the further input data. Here, at least one further parameter of the further trained function may be adjusted based on a comparison of the training determinability parameter with the comparison determinability parameter.

Here, the comparison determinability parameter may be established in a manner analogous with act c) of the proposed method for controlling a medical X-ray device, based on the training object image. The comparison determinability parameter may have all the properties of the determinability parameter that have been described in relation to the method for controlling a medical X-ray device, and vice versa. Furthermore, the comparison determinability parameter may be established by a manual and/or semiautomatic annotation based on the further training object image.

By applying the further trained function to the further input data that is based on the at least one training X-ray image, it is advantageously possible to establish the further training object image. Here, the at least one further parameter of the further trained function may be adjusted, based on a comparison of the training determinability parameter with the comparison determinability parameter. Furthermore, it is possible for the comparison to include, for example, a difference and/or a scalar product and/or a quotient.

As a result, advantageously the accuracy of the further trained function in generating the further training object image may be improved in respect of the determinability of the medical object mapped therein.

In a fourth aspect, the disclosure relates to a medical X-ray device that includes a providing unit. In this case, the medical X-ray device, in particular the providing unit, is configured for carrying out a proposed method for controlling a medical X-ray device. In particular, the medical X-ray device may take the form of a medical C-arm X-ray device and/or a computed tomography system. In this case, the medical X-ray device may furthermore be configured for acquiring and/or receiving and/or providing the at least one X-ray image and/or the object image and/or the determinability parameter.

The advantages of the proposed medical X-ray device correspond substantially to the advantages of the proposed method for controlling a medical X-ray device. Features, advantages, or alternative embodiments that are mentioned in this regard may likewise also apply to the other claimed subject-matter, and vice versa.

In a fifth aspect, the disclosure relates to a training unit that is configured for carrying out the above-mentioned computer-implemented method for providing a trained function and/or for providing a further trained function and its respective aspects. The training unit advantageously includes a training interface and a training processing unit. The training unit is configured for carrying out these methods and their aspects, in that the training interface and the training processing unit are configured for carrying out the corresponding method acts.

In an advantageous embodiment of the proposed training unit, the training interface may be configured for receiving at least one training X-ray image of a region of examination of an object undergoing examination. Furthermore, the training processing unit may be configured for generating a training object image based on the at least one training X-ray image. Moreover, the training processing unit may be configured for establishing a comparison determinability parameter for assessing the determinability of the medical object based on the training object image. Moreover, the training processing unit may be configured for establishing a training determinability parameter by applying a trained function to input data that is based on the at least one training X-ray image. Furthermore, the training processing unit may be configured for adjusting at least one parameter of the trained function based on a comparison of the training determinability parameter with the comparison determinability parameter. Moreover, the training interface may be configured for providing the trained function.

In a further advantageous embodiment of the proposed training unit, the training interface may be configured for receiving at least one training X-ray image of a region of examination of an object undergoing examination. Furthermore, the training processing unit may be configured for generating a comparison object image that is based on the at least one training X-ray image. Moreover, the training processing unit may be configured for generating a further training object image by applying a further trained function to further input data that is based on the at least one training X-ray image. Furthermore, the training processing unit may be configured for adjusting at least one parameter of the further trained function based on a comparison of the further training object image with the comparison object image. Moreover, the training interface may be configured for providing the further trained function.

The advantages of the proposed training unit correspond substantially to the advantages of the proposed computer-implemented method for providing a trained function and/or the proposed computer-implemented method for providing a further trained function. Features, advantages, or alternative embodiments that are mentioned in this regard may likewise also apply to the other claimed subject-matter, and vice versa.

In a sixth aspect, the disclosure relates to a computer program product having a computer program that is directly loadable into a store of a providing unit, having program sections in order to carry out all the acts of the method for controlling a medical X-ray device when the program sections are executed by the providing unit; and/or that is directly loadable into a training store of a training unit, having program sections in order to carry out all the acts of the proposed method for providing a trained function and/or for providing a further trained function and its respective aspects when the program sections are executed by the training unit.

In a seventh aspect, the disclosure relates to a computer-readable storage medium, on which program sections that are readable and executable by a providing unit are stored in order to carry out all the acts of the method for controlling a medical X-ray device when the program sections are executed by the providing unit; and/or on which program sections that are readable and executable by a training unit are stored in order to carry out all the acts of the method for providing a trained function and/or for providing a further trained function and its respective aspects when the program sections are executed by the training unit.

In an eighth aspect, the disclosure relates to a computer program or computer-readable storage medium including a trained function that is provided by a proposed computer-implemented method or one of its aspects.

An implementation that is largely in software form has the advantage that it is possible to upgrade, in a simple manner, even providing units and/or training units that have already been used hitherto, by a software update, in order to operate in the manner according to the disclosure. A computer program product of this kind may, in addition to the computer program, where appropriate include additional constituents such as, for example, documentation and/or additional components and hardware components, such as, for example, hardware keys (e.g., dongles, etc.) for exploiting the software.

BRIEF SUMMARY OF THE DRAWINGS

Exemplary embodiments of the disclosure are illustrated in the drawings and described in more detail below. Like reference characters are used for like features in different figures. In the drawings.

DETAILED DESCRIPTION

Figure 1:
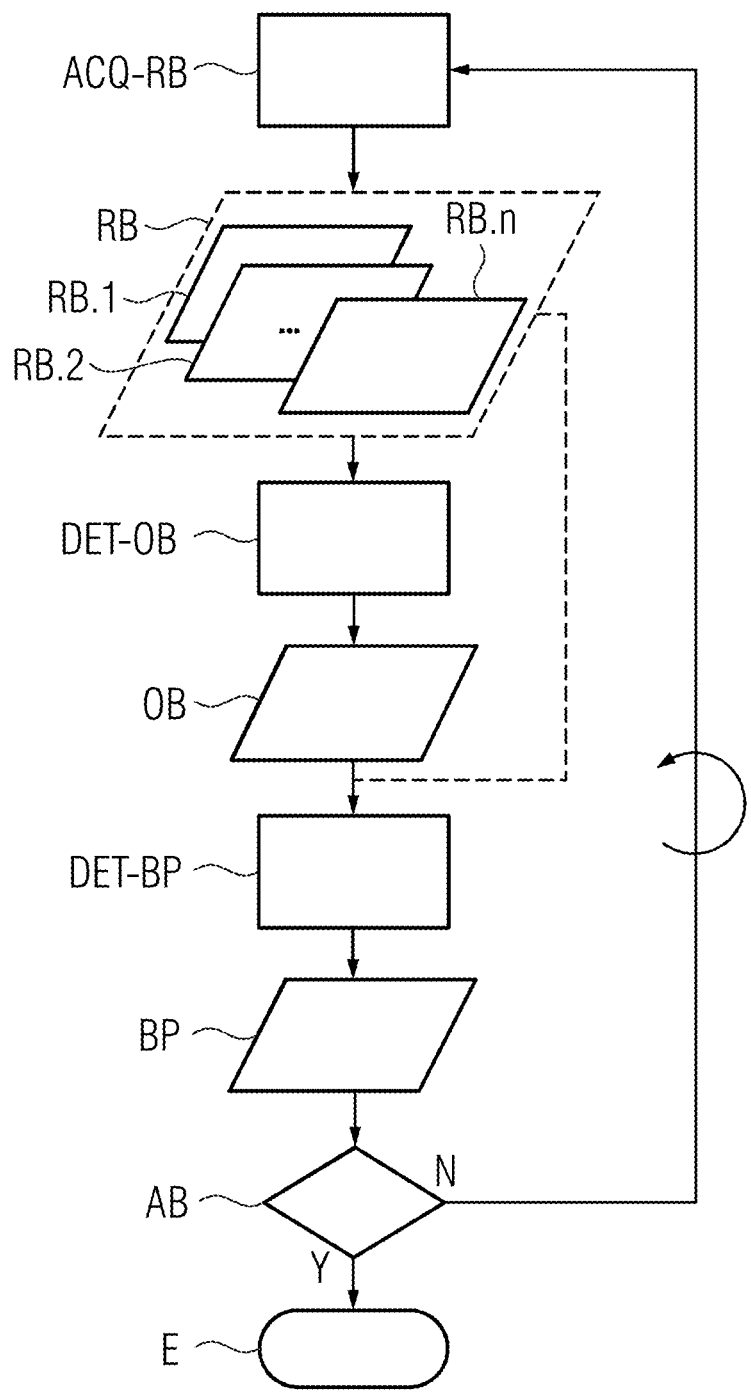
FIGS. 1 to 5 depict schematic illustrations of different embodiments of a proposed method for controlling a medical X-ray device.

FIG. 1 is a schematic illustration of an advantageous embodiment of the proposed method for controlling a medical X-ray device. Here, in act a), at least one X-ray image RB of a region of examination of an object undergoing examination may be acquired by the medical X-ray device, ACQ-RB. Here, a medical object, such as a guide wire and/or catheter and/or endoscope and/or laparoscope and/or implant, in particular a stent, may be arranged in the region of examination. In act b), an object image OB may be generated based on the at least one X-ray image RB, DET-OB. Then, in act c), a determinability parameter BP may be established DET-BP for the purpose of assessing the determinability of the medical object based on the object image OB. Furthermore, the proposed method for controlling the medical X-ray device may be carried out iteratively, beginning at act a), until a termination condition AB occurs based on the most recently established determinability parameter.

Furthermore, generation of the object image DET-OB may include a movement correction and/or registration of the at least one X-ray image RB.

In each iteration of the proposed method, in act a), it is possible in each case to acquire at least one X-ray image RB. After n iterations, it is advantageously possible for at least n X-ray images RB.1, RB.2, . . . RB.n to have been acquired.

The termination condition AB may advantageously include a comparison of the most recently established determinability parameter BP—in particular that established during the current iteration, in act c)—with a predetermined threshold value. In this case, the termination condition AB may occur if the predetermined threshold value is exceeded and/or fallen below and/or reached by the determinability parameter BP, Y. Furthermore, the termination condition AB may have a maximum number of iterations, wherein the termination condition AB occurs if the maximum number of iterations is reached and/or exceeded.

In particular in the case of pulsed emission of X-rays by the X-ray source for the purpose of acquiring the at least one X-ray image RB, ACQ-RB, it is possible for the X-ray source to emit respectively a time-limited X-ray pulse and/or a defined number of X-ray pulses in act a). Here, if the termination condition AB occurs Y, radiation may advantageously be terminated, in particular the pulsed emission of X-rays by the X-ray source may be stopped E.

Figure 2:
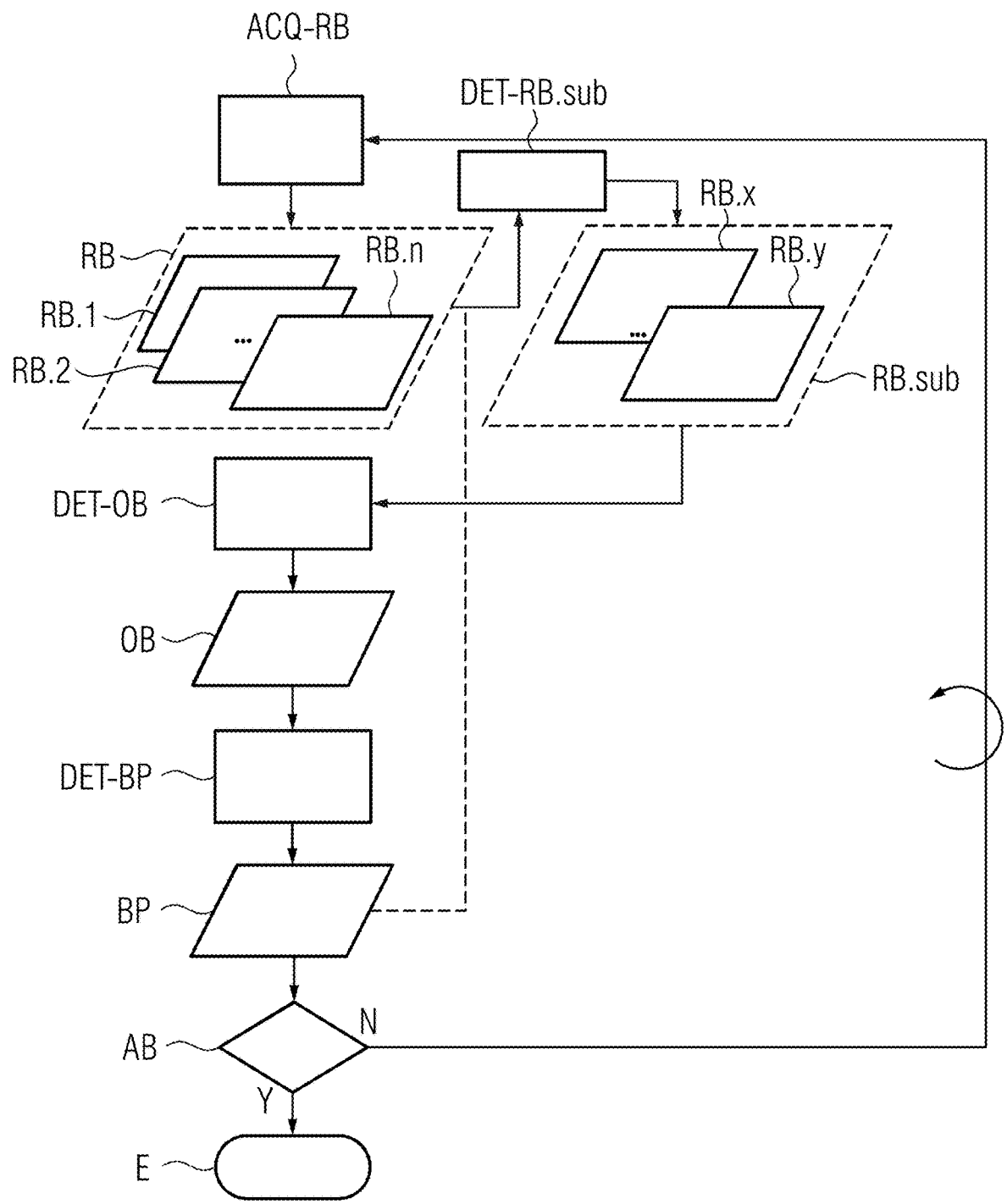

In the embodiment of the proposed method for controlling a medical X-ray device that is illustrated schematically in FIG. 2, at least one subset RB.sub, including at least one X-ray image RB.x, RB.y of the X-ray images RB.1, RB.2, . . . RB.n acquired hitherto, may be determined DET-RB.sub. Here, the object image OB may be generated based on the at least one subset RB.sub of the X-ray images RB.1, RB.2, . . . RB.n acquired hitherto, DET-OB.

Advantageously, the object image OB may be generated by a weighted averaging and/or an adaptive averaging of the at least one subset RB.sub of the X-ray images RB.1, RB.2, . . . RB.n acquired hitherto, DET-OB. Furthermore, determination DET-RB.sub of the at least one subset RB.sub may be carried out based on the determinability parameter BP.

Advantageously, during an iteration of acts a) to c), in each case at least one determinability parameter BP regarding the at least one X-ray image RB—in particular the most recently acquired X-ray image RB—may be established DET-BP based on the object image OB. In this case, the at least one subset RB.sub of the X-ray images RB.1, RB.2, . . . RB.n acquired hitherto for the purpose of generating the object image DET-OB in act b) may furthermore be determined based on the at least one determinability parameter BP. As a result, advantageously the determinability parameter BP of the current iteration may be improved, in particular enhanced. Furthermore, X-ray images RB having image artifacts and/or noise and/or motion artifacts may advantageously be excluded from the at least one subset RB.sub for generation of the object image DET-OB.

Figure 3:
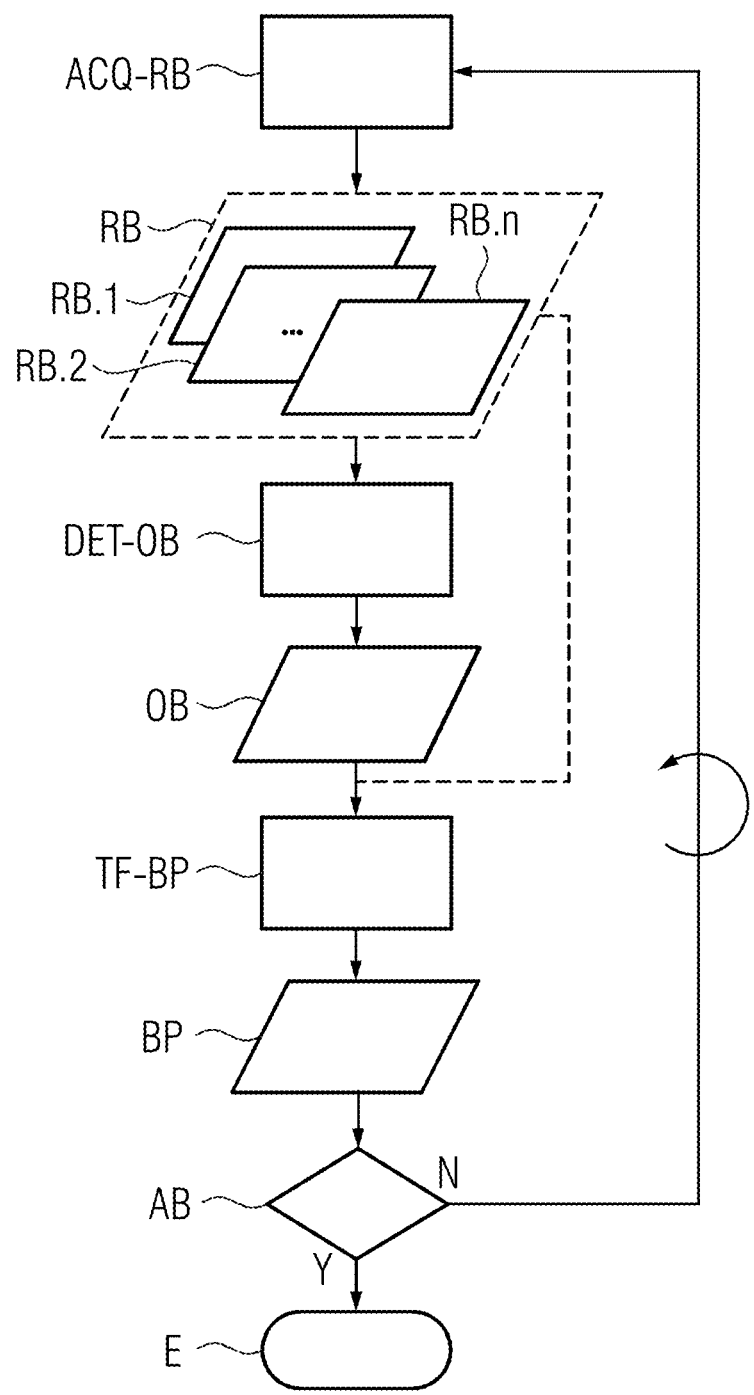

In the embodiment of the proposed method for controlling a medical X-ray device that is illustrated schematically in FIG. 3, the determinability parameter may be established DET-BP in act c) by applying a trained function TF-BP to input data. In this case, the input data may be based on the object image OB. Furthermore, at least one parameter of the trained function TF-BP may be based on a comparison of a training determinability parameter with a comparison determinability parameter.

Figure 4:
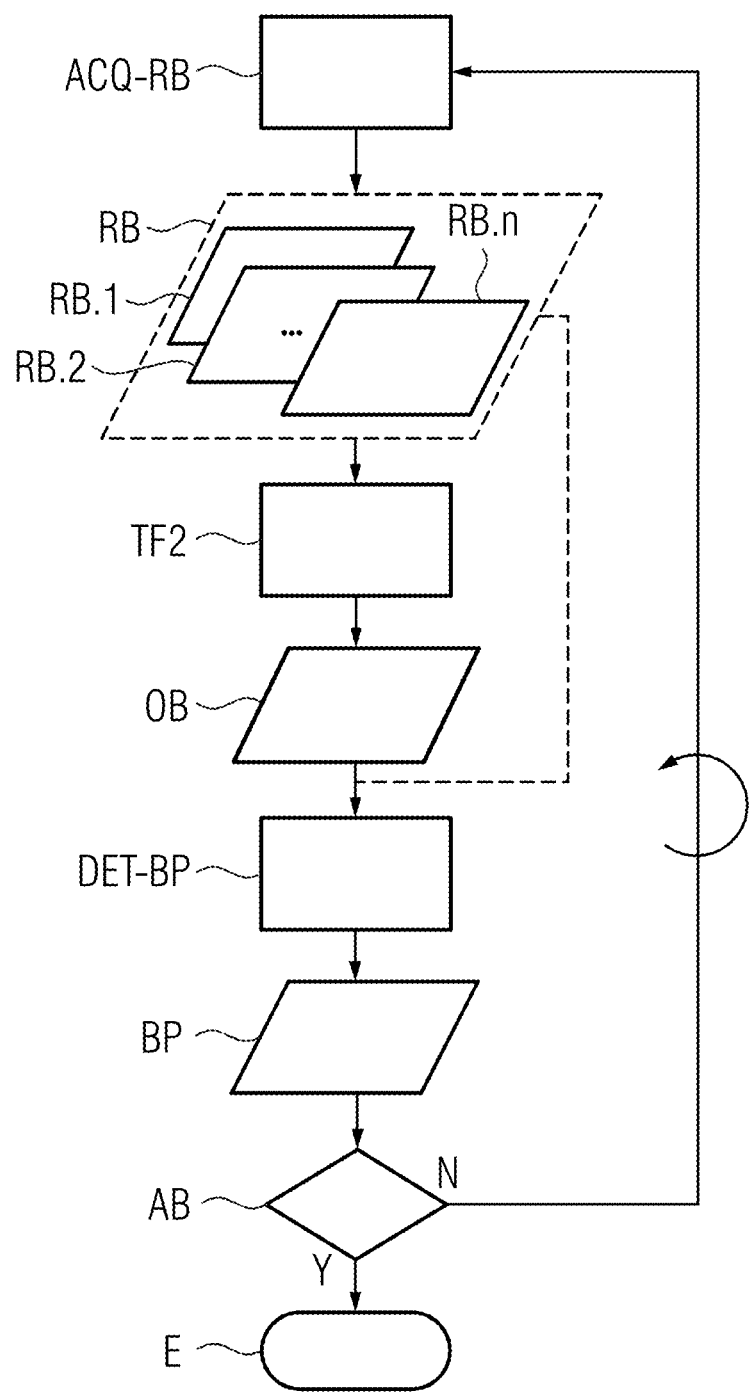

FIG. 4 is a schematic illustration of a further advantageous embodiment of the proposed method for controlling a medical X-ray device. In this case, the object image may be generated DET-OB in act b) by applying a further trained function TF2 to further input data. Here, the further input data may be based on the at least one X-ray image RB. Furthermore, at least one parameter of the trained function TF2 may be based on a comparison of a further training object image with a comparison object image.

Figure 5:
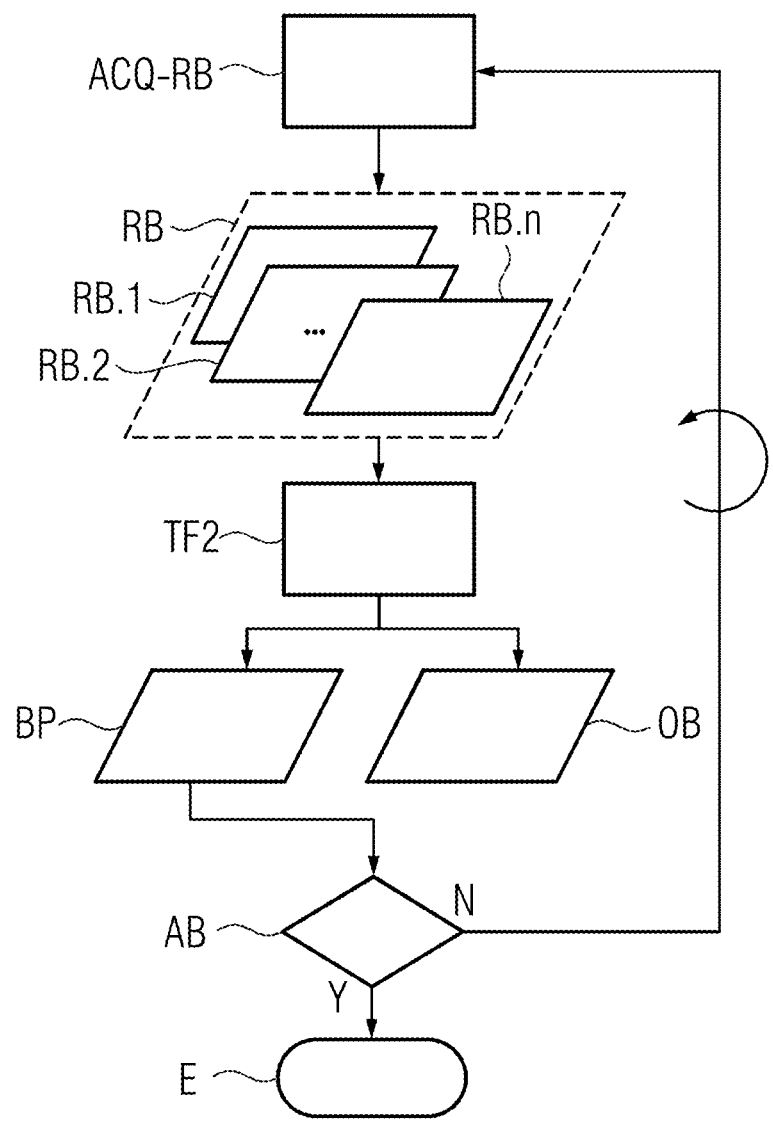

In the embodiment of the proposed method for controlling a medical X-ray device that is illustrated schematically in FIG. 5, the further trained function TF2 may moreover be configured for establishing the determinability parameter DET-BP. In this case, at least one further parameter of the further trained function TF2 may be based on a comparison of a training determinability parameter with a comparison determinability parameter.

Figure 6:
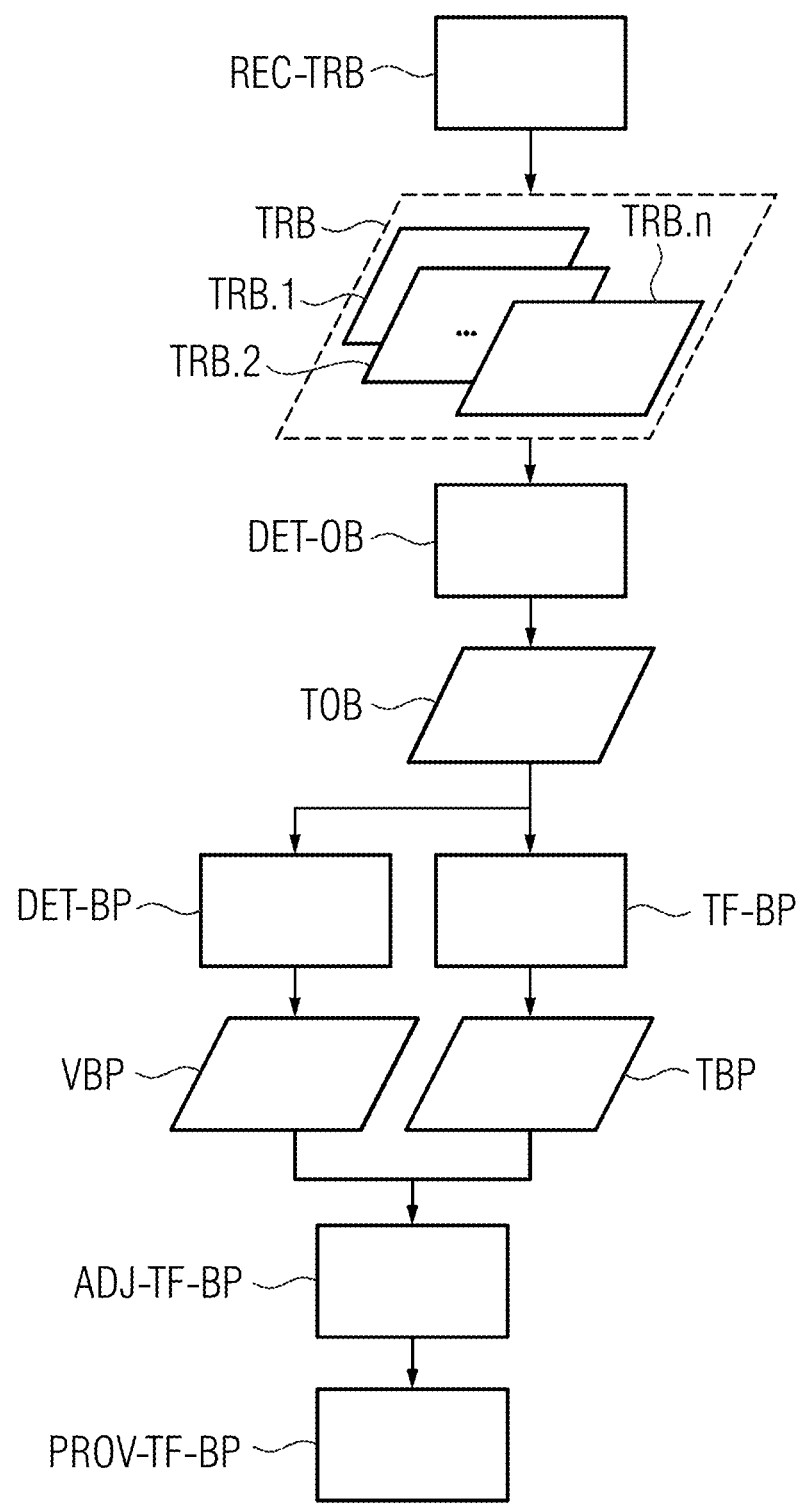
FIG. 6 depicts a schematic illustration of an example of a proposed computer-implemented method for providing a trained function.

FIG. 6 depicts a schematic illustration of an embodiment of the computer-implemented method for providing a trained function TF-BP. Here, in a first act, at least one training X-ray image TRB that maps a region of examination of an object undergoing examination may be received, REC-TRB. In this context, a medical object may be arranged in the region of examination. In a second act, a training object image TOB may be generated based on the at least one training X-ray image TRB, DET-OB. Furthermore, in a third act, a comparison determinability parameter VBP may be established for the purpose of assessing the determinability of the medical object based on the training object image TOB, DET-BP. In a fourth act, which may take place before and/or during and/or after the third act, a training determinability parameter TBP may be established by applying the trained function TF-BP to input data that is based on the at least one training X-ray image TRB. After this, in a fifth act, at least one parameter of the trained function TF-BP may be adjusted based on a comparison of the training determinability parameter TBP with the comparison determinability parameter VBP. In a sixth act, the trained function TF-BP may be provided, PROV-TF-BP.

Figure 7:
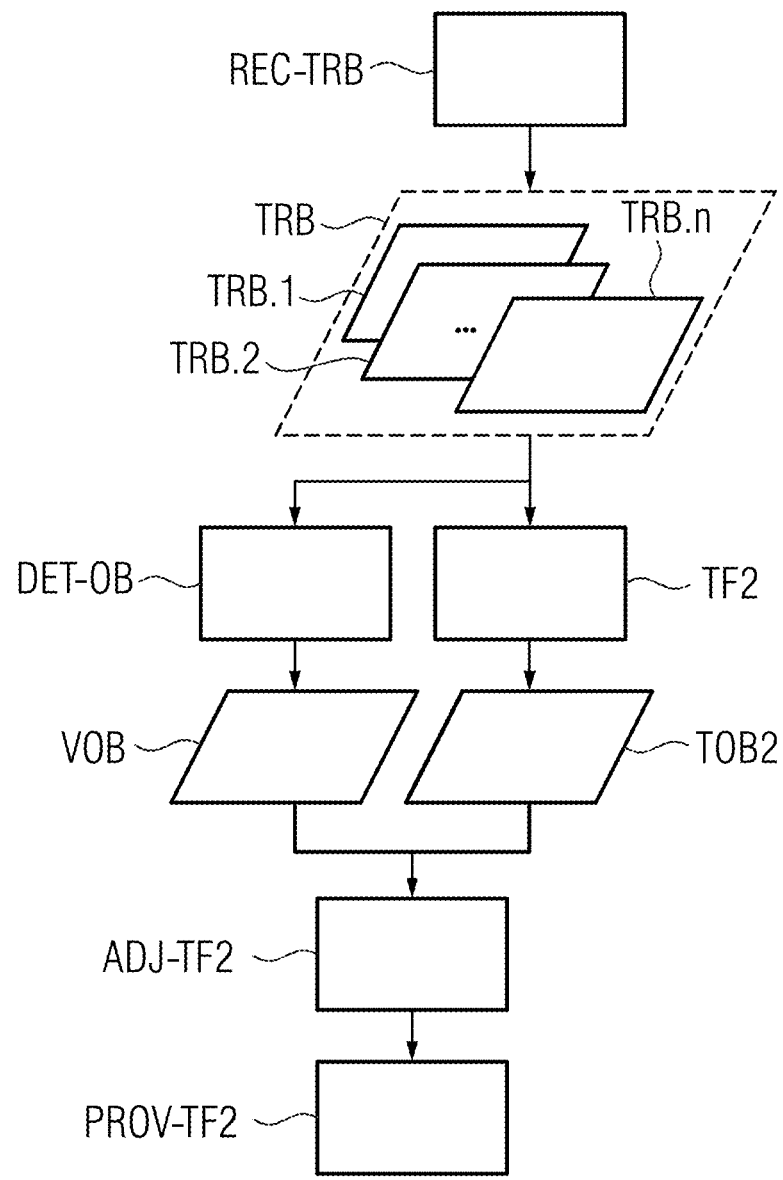
FIGS. 7 and 8 depicts schematic illustrations of different embodiments of a proposed computer-implemented method for providing a further trained function.

FIG. 7 is a schematic illustration of an embodiment of the computer-implemented method for providing a further trained function TF2. In this case, in a first act, at least one training X-ray image TRB may be received of a region of examination of an object undergoing examination, REC-TRB. In this context, a medical object may be arranged in the region of examination. In a second act, a comparison object image VOB may be generated based on the at least one training X-ray image TRB, DET-OB. In a third act, which may take place before and/or during and/or after the second act, a further training object image TOB2 may be generated by applying the further trained function to further input data. Here, the further input data may advantageously be based on the at least one training X-ray image TRB. Furthermore, in a fourth act, at least one parameter of the further trained function TF2 may be adjusted based on a comparison of the further training object image TOB2 with the comparison object image VOB, ADJ-TF2. Then, the further trained function TF2 may be provided in a fifth act, PROV-TF2.

Figure 8:
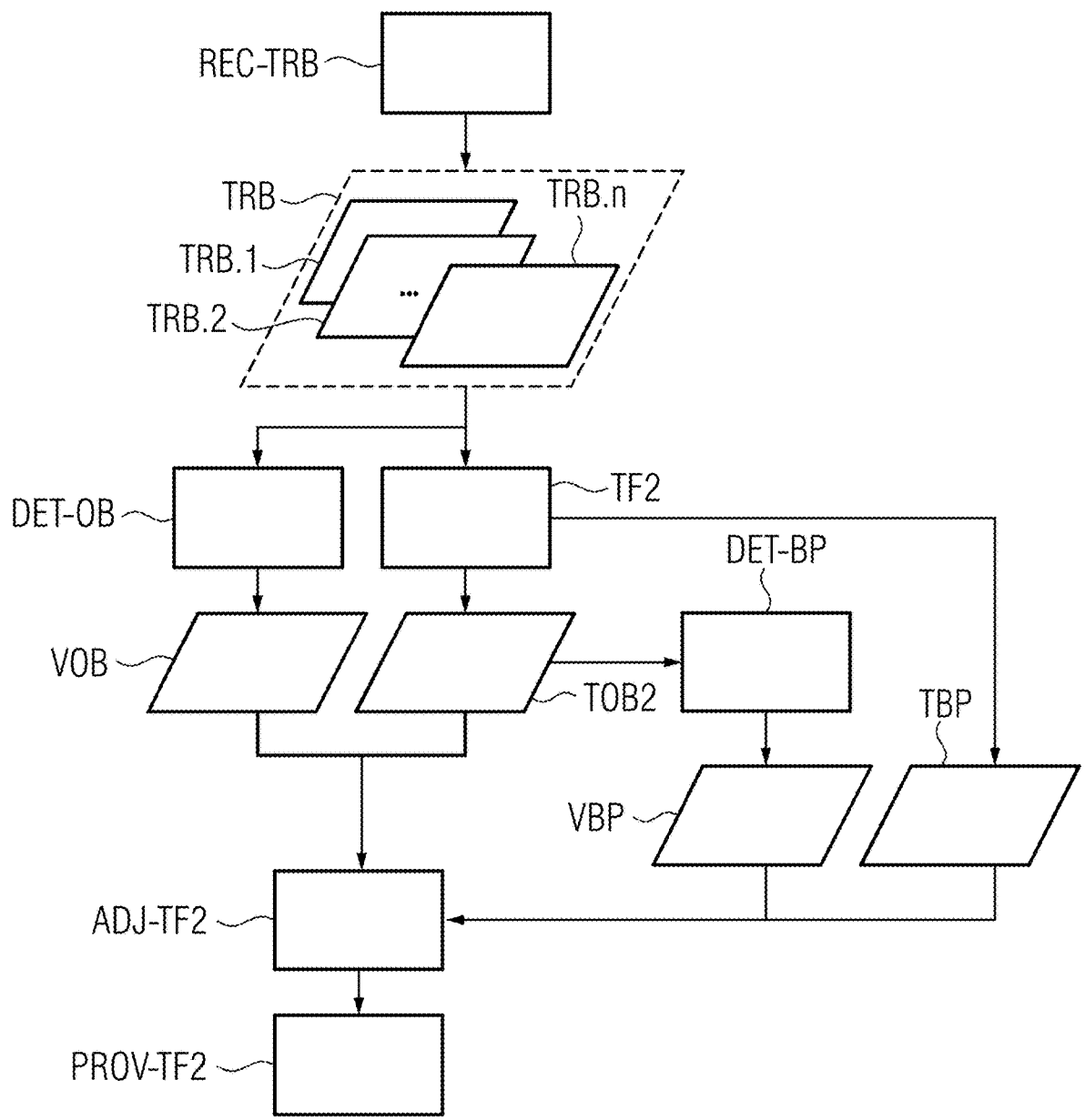

In the embodiment of the proposed computer-implemented method for providing a further trained function TF2 that is illustrated schematically in FIG. 8, a comparison determinability parameter VBP may be established for the purpose of assessing the determinability of the medical object based on the further training object image TOB2, DET-BP. Furthermore, a training determinability parameter TBP may be established by applying the further trained function TF2 to the further input data. Here, at least one further parameter of the further trained function TF2 may be adjusted based on a comparison of the training determinability parameter TBP with the comparison determinability parameter VBP, ADJ-TF2.

Figure 9:
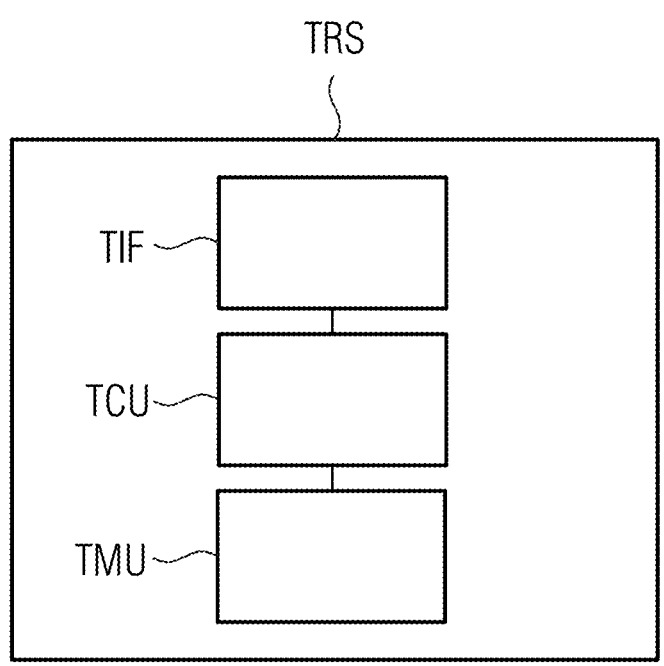
FIG. 9 depicts a schematic illustration of an example of a training unit.

FIG. 9 schematically illustrates a proposed training unit TRS including a training interface TIF, a training processing unit TCU and a training storage unit TMU. The training unit TRS may be configured for carrying out a proposed computer-implemented method for providing a trained function, PROV-TF, and/or a proposed computer-implemented method for providing a further trained function PROV-TF2 and its respective aspects in that the training interface TIF and the training processing unit TCU are configured for carrying out the corresponding method acts.

In an advantageous embodiment of the proposed training unit TRS, the training interface TIF may be configured for receiving REC-TRB the at least one training X-ray image TRB from the region of examination of the object undergoing examination. Furthermore, the training processing unit TCU may be configured for generating DET-OB the training object image TOB based on the at least one training X-ray image TRB. Moreover, the training processing unit TCU may be configured for establishing DET-BP the comparison determinability parameter VBP for the purpose of assessing the determinability of the medical object based on the training object image TOB. Moreover, the training processing unit TCU may be configured for establishing the training determinability parameter TBP by applying the trained function TF-BP to input data that is based on the at least one training X-ray image TRB. Furthermore, the training processing unit TCU may be configured for adjusting ADJ-TF-BP the at least one parameter of the trained function TF-BP based on a comparison of the training determinability parameter TBP with the comparison determinability parameter VBP. Moreover, the training interface TIF may be configured for providing PROV-TF-BP the trained function TF-BP.

In a further advantageous embodiment of the proposed training unit TRS, the training interface TIF may be configured for receiving REC-TRB the at least one training X-ray image TRB from the region of examination of the object undergoing examination. Furthermore, the training processing unit TCU may be configured for generating DET-VOB the comparison object image VOB based on the at least one training X-ray image TRB. Moreover, the training processing unit TCU may be configured for generating the further training object image TOB2 by applying the further trained function TF2 to the further input data that is based on the at least one training X-ray image TRB. Furthermore, the training processing unit TCU may be configured for adjusting ADJ-TF2 the at least one parameter of the further trained function TF2 based on a comparison of the further training object image TOB2 with the comparison object image VOB. Moreover, the training interface TIF may be configured for providing PROV-TF2 the further trained function TF2.

A training interface TIF may be a hardware or a software interface (for example, a PCI bus, USB, or FireWire). A training processing unit TCU may include hardware elements or software elements, for example, a microprocessor or a so-called FPGA (field programmable gate array). A training storage unit TMU may take the form of a random access memory (RAM) or non-volatile mass storage (e.g., hard disk, USB stick, SD card, solid state disk).

The training interface TIF may include a plurality of subinterfaces that carry out different acts of the respective methods. In other words, the training interface TIF may also be composed of a multiplicity of training interfaces TIF. The training processing unit TCU may include a plurality of subinterfaces that carry out different acts of the respective methods. In other words, the training processing unit TCU may also be composed of a multiplicity of training processing units TCU.

The training unit TRS may be a computer, a microcontroller, or an integrated circuit. As an alternative, the training unit TRS may be a real or virtual group of computers (a technical term for a real group is a cluster, and a technical term for a virtual group is a cloud). The training unit TRS may also take the form of a virtual system that is implemented on a real computer or a real or virtual group of computers (virtualization).

Figure 10:
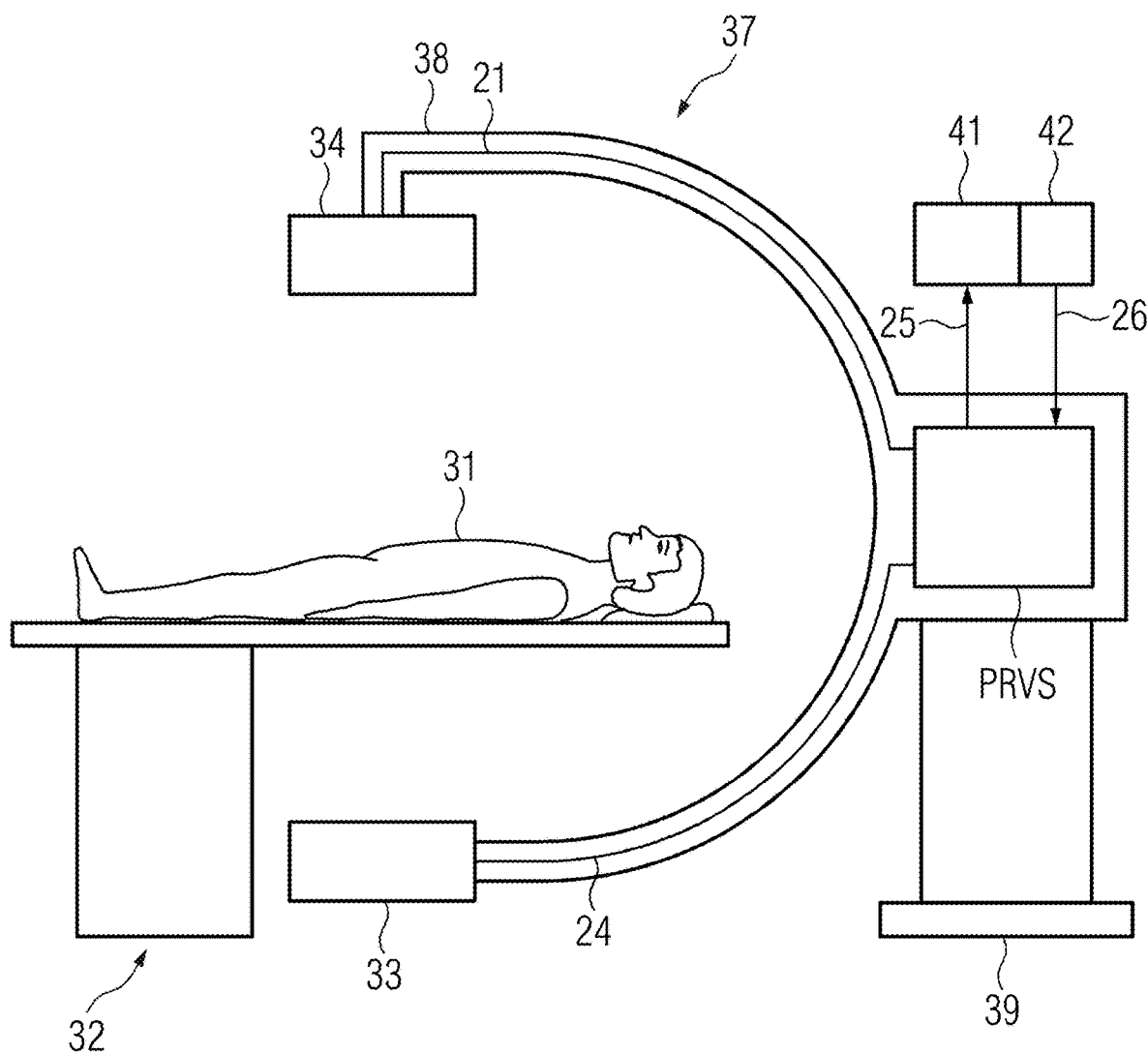
FIG. 10 depicts a schematic illustration of an example of a medical C-arm X-ray device.

FIG. 10 is a schematic illustration, providing an example of a proposed medical imaging device, of a medical C-arm X-ray device 37. Here, the medical C-arm X-ray device 37 may advantageously include a proposed providing unit PRVS for controlling the medical X-ray device 37. In this case, the medical imaging device 37, (e.g., the proposed providing unit PRVS), is configured for carrying out a proposed method for controlling the medical X-ray device 37.

Here, the medical C-arm X-ray device 37 moreover includes a detector unit 34 and an X-ray source 33. For the purpose of acquiring the at least one X-ray image RB, the arm 38 of the C-arm X-ray device 37 may be mounted such that it is movable about one or more axes. Furthermore, the medical C-arm X-ray device 37 may include a motion apparatus 39 that enables movement of the C-arm X-ray device 37 in space.

For the purpose of acquiring the at least one X-ray image RB of the region of examination of the object undergoing examination 31, which is arranged on a patient supporting facility 32, the providing unit PRVS may transmit a signal 24 to the X-ray source 33. Then, the X-ray source 33 may emit a bundle of X-rays, in particular a cone beam and/or fan beam and/or parallel beam. When, after interaction with the region of examination of the object undergoing examination 31 that is to be mapped, the X-ray bundle impinges on a surface of the detector unit 34, the detector unit 34 may transmit a signal 21 to the providing unit PRVS. The providing unit PRVS may receive the at least one X-ray image RB, for example, by way of the signal 21.

Moreover, the medical C-arm X-ray device 37 may include an input unit 42, (e.g., a keyboard), and/or a representation unit 41, (e.g., a monitor and/or display). The input unit 42 may be integrated in the representation unit 41, for example, in the case of a capacitive input display. In this case, as a result of an input at the input unit 42 performed by a member of the operating personnel, an in particular additional control of the medical C-arm X-ray device 37—in particular of the proposed method for controlling the medical X-ray device 37—may be enabled. For this, the input unit 42 may transmit a signal 26 to the providing unit PRVS.

Furthermore, the representation unit 41 may be configured for displaying information and/or graphical representations of information of the medical imaging device 37 and/or the providing unit PRVS and/or further components. For this, the providing unit PRVS may transmit a signal 25 to the representation unit 41. In particular, the representation unit 41 may be configured for displaying a graphical representation of the at least one X-ray image RB and/or the at least one subset RB.sub of the X-ray images that have been acquired hitherto and/or the object image OB and/or the determinability parameter BP.

The providing unit PRVS may be a computer, a microcontroller, or an integrated circuit. As an alternative, the providing unit PRVS may be a real or virtual group of computers (a technical term for a real group is a cluster, and a technical term for a virtual group is a cloud). The providing unit PRVS may also take the form of a virtual system that is implemented on a real computer or a real or virtual group of computers (virtualization).

The schematic representations in the described figures give no indication whatever of scale or relative size.

Finally, it should be pointed out again that the methods described in detail above and the apparatuses illustrated are merely exemplary embodiments, which may be modified by those skilled in the art in the greatest variety of ways without departing from the scope of the disclosure. Furthermore, the use of the indefinite articles "a" and "an" does not rule out the possibility that the features concerned may also be present a plurality of times. Likewise, the terms "unit" and "element" do not rule out the possibility that the components concerned include a plurality of cooperating sub-components, which where appropriate may also be spatially separated from one another.

It is to be understood that the elements and features recited in the appended claims may be combined in different ways to produce new claims that likewise fall within the scope of the present disclosure. Thus, whereas the dependent claims appended below depend from only a single independent or dependent claim, it is to be understood that these dependent claims may, alternatively, be made to depend in the alternative from any preceding or following claim, whether independent or dependent, and that such new combinations are to be understood as forming a part of the present specification.

Although the disclosure has been illustrated and described in detail with reference to the exemplary embodiments, it is not limited by the disclosed examples and a person skilled in the art may derive other variations herefrom without departing from the scope the disclosure.

The invention claimed is:

1. A method for controlling a medical X-ray device, the method comprising:
acquiring at least one X-ray image of a region of examination of an object undergoing examination by the medical X-ray device, wherein a medical object is arranged in the region of examination;
generating an object image based on the at least one X-ray image; and
establishing a determinability parameter for assessing a determinability of the medical object based on the object image,
wherein the method is carried out iteratively, beginning with the acquiring of an X-ray image, until a termination condition occurs based on a most recently established determinability parameter.

2. The method of claim 1, wherein the at least one acquired X-ray image comprises a plurality of X-ray images, and
wherein the object image is generated by averaging at least one subset of the plurality of X-ray images.

3. The method of claim 2, wherein the at least one subset of the plurality of X-ray images for generating the object image is determined based on the determinability parameter.

4. The method of claim 3, wherein the termination condition comprises a comparison of the determinability parameter with a predetermined threshold value.

5. The method of claim 4, wherein the generating of the object image comprises a movement correction of the at least one X-ray image, a registration of the at least one X-ray image, or a combination thereof.

6. The method of claim 5, wherein the determinability parameter is established by applying a trained function to input data,
wherein the input data is based on the object image, and
wherein at least one parameter of the trained function is based on a comparison of a training determinability parameter with a comparison determinability parameter.

7. The method of claim 6, wherein the object image is generated by applying a further trained function to further input data,
wherein the further input data is based on the at least one X-ray image, and
wherein at least one parameter of the further trained function is based on a comparison of a further training object image with a comparison object image.

8. The method of claim 7, wherein the further trained function is configured for establishing the determinability parameter, and
wherein at least one further parameter of the further trained function is based on a comparison of a training determinability parameter with a comparison determinability parameter.

9. The method of claim 1, wherein the termination condition comprises a comparison of the determinability parameter with a predetermined threshold value.

10. The method of claim 1, wherein the generating of the object image comprises a movement correction of the at least one X-ray image, a registration of the at least one X-ray image, or a combination thereof.

11. The method of claim 1, wherein the determinability parameter is established by applying a trained function to input data,
   wherein the input data is based on the object image, and
   wherein at least one parameter of the trained function is based on a comparison of a training determinability parameter with a comparison determinability parameter.

12. The method of claim 1, wherein the object image is generated by applying a further trained function to further input data,
   wherein the further input data is based on the at least one X-ray image, and
   wherein at least one parameter of the further trained function is based on a comparison of a further training object image with a comparison object image.

13. The method of claim 12, wherein the further trained function is configured for establishing the determinability parameter, and
   wherein at least one further parameter of the further trained function is based on a comparison of a training determinability parameter with a comparison determinability parameter.

14. A medical X-ray device comprising:

a providing unit, wherein the medical X-ray device is configured to acquire at least one X-ray image of a region of examination of an object undergoing examination by the medical X-ray device, wherein a medical object is arranged in the region of examination, wherein the providing unit is configured to:
   generate an object image based on the at least one acquired X-ray image; and
   establish a determinability parameter, for assessing a determinability of the medical object based on the object image, wherein the medical X-ray device and the providing unit of the medical X-ray device are configured to iteratively acquire X-ray images, generate object images, and establish determinability parameters until a termination condition occurs based on the most recently established determinability parameter.

* * * * *